United States Patent [19]

Lardon et al.

[11] 4,438,282

[45] Mar. 20, 1984

[54] PREPARATION OF SULFIDES

[75] Inventors: Hartmut Lardon, Ludwigshafen; Guenther Seybold, Neuhofen, both of Fed. Rep. of Germany

[73] Assignee: BASF Aktiengesellschaft, Ludwigshafen, Fed. Rep. of Germany

[21] Appl. No.: 391,105

[22] Filed: Jun. 23, 1982

[30] Foreign Application Priority Data

Jul. 1, 1981 [DE] Fed. Rep. of Germany ....... 3125920

[51] Int. Cl.³ .................... C07C 149/30; C07C 149/10
[52] U.S. Cl. ........................ 568/58; 260/464; 260/465 F; 260/465 G; 260/465 H; 260/465 R; 260/465.1; 260/465.6; 260/465.7; 260/465.8 R; 549/13; 549/28; 549/61; 549/62; 549/63; 549/68; 549/83; 564/250; 564/251; 564/259; 568/38; 568/39; 568/44; 568/45; 568/49; 568/53; 568/54; 568/56; 568/59; 568/60
[58] Field of Search ....................... 564/250, 251, 259; 568/38, 56, 58, 60, 39, 44, 45, 49, 59, 53, 54; 260/464, 465 F, 465 G, 465 H, 465 R, 465.1, 465.6, 465.7, 465.8; 549/13, 28, 61, 62, 63, 68, 83

[56] References Cited

U.S. PATENT DOCUMENTS

| | | | |
|---|---|---|---|
| 1,892,972 | 1/1933 | Urbain | 564/251 |
| 2,930,750 | 3/1960 | Wendland | 208/236 |
| 3,338,965 | 8/1967 | Belden et al. | 564/259 |
| 3,655,760 | 4/1972 | de Rooij et al. | 564/259 |
| 3,932,471 | 1/1976 | Magee | 424/300 |
| 4,028,413 | 6/1977 | Magee | 260/566 A |
| 4,118,389 | 10/1978 | Magee | 424/327 |
| 4,128,581 | 12/1978 | Magee | 260/566 AC |

FOREIGN PATENT DOCUMENTS 2216838 11/1972 Fed. Rep. of Germany.

OTHER PUBLICATIONS

Inorganic Chemistry, 9, 211–215, (1970).
Electrochimica Acta, 12, 767–772, (1967).
Chem. Ber. 42, 2282–2291, (1909).
ibid. 43, 1401–1412, (1910).
Chem. Ber. 114, 822–824, (1981).
Houben-Weyl, Method. der Org. Chem. 9, 218–220, (1955).
Synthesis 1979, 58–59.
Synthesis 1980, 67–68 and 221.
Synthesis 1981, 141–142.
J. Amer. Chem. Soc. 91, 682–687, (1969).
Org. Prep. Proc. Int. 9, 64–83, (1977).

*Primary Examiner*—Donald G. Daus
*Assistant Examiner*—M. C. Eakin
*Attorney, Agent, or Firm*—John H. Shurtleff

[57] ABSTRACT

Sulfides prepared by reacting a sulfoxide with a hydrazine or hydroxylamine derivative or a quaternary salt thereof are useful starting materials for the preparation of drugs, pesticides and dyes.

21 Claims, No Drawings

PREPARATION OF SULFIDES

The present invention relates to a process for the preparation of sulfides by reacting a sulfoxide with a hydrazine or hydroxylamine derivative or a quaternary salt thereof.

Numerous methods for reducing sulfoxides to sulfides are described in Org. Prep. Proc. Int. 9 (1977), 64–83. However, the conventional processes either give moderate yields or employ chemicals which are expensive or difficult to obtain.

We have found that sulfides of the formula $$R^1-S-R^2 \qquad \text{I}$$

where $R^1$ and $R^2$ can be identical or different and each is an aliphatic, cycloaliphatic, araliphatic or aromatic radical, or $R^1$ and $R^2$ together with the adjacent sulfur atom are also members of a heterocyclic ring, are advantageously obtained by reduction of sulfoxides when a sulfoxide of the formula $$R^1-\overset{\overset{O}{\|}}{S}-R^2 \qquad \text{II}$$

where $R^1$ and $R^2$ have the above meanings, is reacted with an amine derivative of the formula $$H_2N-XR^2 \qquad \text{III}$$

where X is oxygen or the radical $$-\overset{\overset{H}{|}}{N}-, \qquad \text{III}$$

and $R^3$ is hydrogen, a sulfonic acid group or an acyl radical, or with its ammonium salt, the carbonyl groups which may be present in $R^1$ and $R^2$ being converted to ketoximes in the case in which $R^3$ is hydrogen and X is oxygen, and to hydrazones in the case in which $R^3$ is hydrogen and X is the radical $$-\overset{\overset{}{|}}{\underset{H}{N}}-.$$

Where hydroxylamine-O-sulfonic acid and dimethylsulfoxide are used, the reaction may be represented by the following equation:

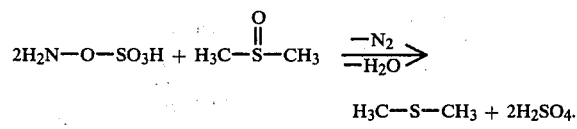

$$2H_2N-O-SO_3H + H_3C-\overset{\overset{O}{\|}}{S}-CH_3 \xrightarrow[-H_2O]{-N_2} H_3C-S-CH_3 + 2H_2SO_4.$$

Compared to the known processes, the process according to the invention uses simpler and more economical starting materials and gives a large number of sulfides in good yield and purity by a simpler and more economical route. All these advantages are surprising in view of the prior art.

The starting materials II and III can be reacted with one another in the stoichiometric amounts or in excess, advantageously using from 1 to 4, preferably from 2 to 3, equivalents of starting material III, or of its ammonium salt, per mole of starting material II. Preferred starting materials II and, accordingly, preferred end products I are those in which formulae $R^1$ and $R^2$ can be identical or different groups and each is alkyl of 1–8 carbon atoms, cycloalkyl of 5–8 carbon atoms, aralkyl or alkylaryl of 7–12 carbon atoms, or phenyl, or $R^1$ and $R^2$ together with the adjacent sulfur atom also form a 5-membered or 6-membered heterocyclic ring. The above groups can also be substituted by groups which are inert under the reaction conditions, eg. oxo, cyano, and eg. alkyl or alkoxy, each of 1–7 C atoms. If $R^1$ and/or if desired $R^2$ are each a ketone and $R^3$ is hydrogen, in addition to the reaction according to the invention the keto group is converted into the ketoxime group in the case in which X is O and into the hydrazone group in the case in which X is NH.

Thus, the following sulfoxides are examples of suitable starting materials II: dimethyl-, dipropyl-, diisopropyl-, dibutyl-, diisobutyl-, di-sec.-butyl-, di-tert.-butyl-, dicyclohexyl-, dicyclopentyl-, dibenzyl-, diphenyl-, di-o-methylphenyl-, di-m-methylphenyl-, di-p-methylphenyl-, tetramethylene- and pentamethylenesulfoxide; 3,3-dimethyl-1-methylsulfinyl-2-butanone, 2-methylsulfinylacetophenone, 4'-methoxy-2-methylsulfinylacetophenone, 4'-methyl-2-methylsulfinylacetophenone, 4'-nitro-2-methylsulfinylacetophenone, 4'-chloro-2-methylsulfinylacetophenone, 1-methylsulfinyl-2-propanone and 1-methylsufinyl-3-butanone.

The hydrazine or hydroxylamine used as starting material III can be substituted by a sulfonic acid or an acyl group, but as a rule the unsubstituted hydrazine or hydroxylamine is used.

The acyl radicals of starting material III can be aliphatic, cycloaliphatic, araliphatic or aromatic radicals, specific examples being methylcarbonyl, ethylcarbonyl, propylcarbonyl, isopropylcarbonyl, butylcarbonyl, isobutylcarbonyl, sec.-butylcarbonyl, tert.-butylcarbonyl, cyclohexylcarbonyl, phenylmethylcarbonyl and phenylcarbonyl.

The hydroxylamine or hydrazine is advantageously used in the form of its salts. Examples of suitable salts are the chloride, nitrate, sulfate, formate and acetate of hydroxylamine or hydrazine. If the starting material II is a β-ketosulfoxide, the reaction is carried out as a rule at a pH from 6 to 8, preferably 7.

The reaction can advantageously be carried out at from 20° to 150° C., preferably from 55° to 145° C., under atmospheric or superatmospheric pressure, either continuously or batchwise.

The reaction can be carried out in the presence of a solvent. Advantageously, a solvent which is inert under the reaction conditions is used. Examples of suitable solvents are ethers, eg. ethyl propyl ether, methyl tert.-butyl ether, n-butyl ethyl ether, di-n-butyl ether, diisobutyl ether, diisoamyl ether, diisopropyl ether, cyclohexyl methyl ether, diethyl ether, ethylene glycol dimethyl ether, tetrahydrofuran and dioxane; esters, eg. methyl acetate, n-propyl acetate, methyl propionate, butyl acetate, ethyl formate, methyl phthalate, methyl benzoate, ethyl acetate and phenyl acetate; alkanols and cycloalkanols, eg. ethanol, methanol, n-butanol, isobutanol, tert.-butanol, glycol, glycerol, n-propanol, isopropanol, amyl alcohol, cyclohexanol, 2-methyl-4-pentanol, ethylene glycol monoethyl ether, 2-ethylhexanol, methylglycol, n-hexanol, isohexyl alcohol, isoheptyl alcohol, n-heptanol, ethylbutanol, nonyl alcohol, dodecyl alcohol and methylcyclohexanol, in particular those of 1 to 4 carbon atoms; substituted amides, eg. dimethylformamide; water; halohydrocarbons, in particular chlorohydrocarbons, eg. tetrachloroethylene, 1,1,2,2,-and 1,1,1,2-tetrachloromethane, amyl chloride, dichloroproane, methyl chloride, dichlorobutane, chloroform, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3- and iso-butyl chloride, chlorobenzene, o-, p- and m-dichlorobenzene, o-, m- and p-chlorotoluene and 1,2,4-trichlorobenzene. Ethanol, isobutanol, dimethylformamide, tetrahydrofuran, dimethoxyethane and n-butanol, and appropriate mixtures, are preferred. The solvent is advantageously used in an amount of from 100 to 10,000 percent by weight, preferably from 100 to 2,000 percent by weight, based on starting material II. Advantageously, a mixture with water and another solvent, for example, an alkanol is chosen, the amount of water advantageously being from 0 to 80 percent by weight, based on the total mixture.

The reaction can be carried out as follows: a mixture of starting material II and starting material III (or its quaternary salt) is kept at the above temperature for from 1 to 32, preferably from 1 to 7, hours. The end product is then isolated in a conventional manner, for example by distillation, extraction or filtration.

The sulfides obtained by the process of the invention are useful starting materials for the preparation of drugs, pesticides and dyes. The process is particularly suitable for preparing ketoxime sulfides, which are useful intermediates for insecticides and other active compounds, and the ketosulfoxides used as starting materials are reduced and oximated in one step by the method according to the invention.

Regarding the use of these compounds, reference may be made to the above publication.

In the Examples which follow, parts are by weight.

EXAMPLE 1

26 parts of dimethylsulfoxide are added to 64.8 parts of hydroxylammonium sulfate at 120° C. in the course of one hour, and stirring is continued for one hour at the same reaction temperature. The dimethyl sulfide formed begins to distill off into a cooled vessel during the addition. After the reaction is complete, the distillate is distilled again, and 15.9 parts (77% of theory) of dimethyl sulfide pass over at 37° C.

EXAMPLE 2

4.6 parts of dimethylsulfoxide are slowly added to 22.6 parts of hydroxylamine-O-sulfonic acid at 70° C. in the course of 10 minutes, and stirring is continued for one hour at 100° C. 2.2 parts (60% of theory) of dimethyl sulfide of boiling point 37° C. are isolated.

EXAMPLE 3

Using a procedure similar to that described in Example 1, 70 parts of hydroxylammonium chloride are first suspended in 50 parts of n-butanol, and thereafter a solution of 39 parts of dimethylsulfoxide in 80 parts of n-butanol is added at 120° C. 23.5 parts (76% of theory) of dimethyl sulfide of boiling point 37° C. are obtained.

EXAMPLE 4

78 parts of dimethylsulfoxide are added to 52.5 parts of hydrazine dihydrochloride at 60° C. in the course of 2 hours, and stirring is continued for one hour at 90° C. The dimethyl sulfide formed begins to distill off into a cooled vessel before the addition has ended. After the reaction is complete, the distillate is distilled again, and 60.9 parts (98% of theory) of dimethyl sulfide pass over at 37° C.

EXAMPLES 5 TO 10

Using a procedure similar to that described in Example 1 or 4, the sulfoxides listed below are reduced either by a hydrazine III (in the form of its salt) or by a hydroxylamino III (in the form of its salt). 100 parts of water are added to the reaction mixture, the resulting mixture is extracted with three times 100 parts of chloroform, and the extract is distilled.

| Example No. | Starting material | Yield of end product in % of theory using a hydroxyl- amine III | Yield of end product in % of theory using a hydra- zine III | Boiling point of the end product in °C./mbar |
|---|---|---|---|---|
| 5 | Di-n-propylsulfoxide | 71 | 93 | 142–143/1 000 |
| 6 | Di-iso-propylsulfoxide | 76 | 91 | 120–121/1 000 |
| 7 | Di-n-butylsulfoxide | 80 | 95 | 85–86/20 |
| 8 | Di-tert.-butylsulfoxide | 70 | 89 | 40–41/20 |
| 9 | Tetramethylen-sulfoxide | 72 | 92 | 119–120/1 000 |
| 10 | Dibenzylsulfoxide | 70 | 90 | 130–131/0.45 |

The sulfides formed are characterized by comparison with the spectroscopic and physical data of authentic materials.

EXAMPLE 11

56.4 parts of 3,3-dimethyl-1-methylsulfinyl-2-butanone, 128.6 parts of hydroxylammonium chloride, 98.6 parts of sodium carbonate, 230 parts of water and 400 parts of iso-butanol at pH 7 are stirred for 32 hours at 95° C. The mixture is cooled to room temperature, after which the aqueous phase is discarded and the organic phase is fractionally distilled. 47.9 parts (85% of theory) of 3,3-dimethyl-1-methylthio-2-butanone oxime of refractive index $n_D^{24}=1.5008$ pass over at 85°–86° C./0.9 mbar.

|  | C | H | O | N | S |
|---|---|---|---|---|---|
| calculated: | 52.1 | 9.4 | 9.9 | 8.7 | 19.9 |
| found: | 53.5 | 9.5 | 10.0 | 8.5 | 19.2 |

EXAMPLE 12

18.2 parts of 2-methylsulfinylacetophenone, 29.6 parts of hydroxylammonium sulfate, 19.2 parts of sodium carbonate, 80 parts of water and 100 parts of ethanol are refluxed for 17 hours. Thereafter, the greater part of the solvent is distilled off, 300 parts of water are added, and the mixture is extracted with three times 70 parts of ethyl acetate. The combined organic phases are dried over sodium sulfate, freed of solvent under reduced pressure, and recrystallized from cyclohexane. 8.6 parts (48% of theory) of 2-methylthioacetophenone oxime of melting point 59°–60° C. are obtained.

EXAMPLE 13

A mixture of 10.5 parts of methylphenylsulfoxide and 21 parts of hydroxylammonium chloride is stirred for 5 hours at 95° C. The reaction mixture is cooled to room temperature, after which it is stirred with 100 parts of methylene chloride, insoluble constituents are filtered off and washed several times with methylene chloride, and the combined filtrates are concentrated under reduced pressure. From the residue, 7.0 parts (74% of theory) of methyl phenyl sulfide are distilled off at 45° C./0.8 mbar.

EXAMPLE 14

A mixture of 15.15 parts of diphenylsulfoxide and 8.4 parts of hydrazine dichloride is stirred for 21 hours at 140° C. The reaction mixture is cooled to room temperature, after which 200 parts of water are added, the mixture is extracted with four times 70 parts of chloroform, and the combined organic phases are dried over sodium sulfate. The solvent is removed, and thereafter 9.9 parts (71% of theory) of diphenyl sulfide are distilled off at 92°–95° C./0.1 mbar.

EXAMPLES 15 AND 16

Using procedures similar to those described in Example 13 (hydroxylamine) and Example 14 (hydrazine), the following sulfoxides are reduced by both methods and are purified by recrystallization instead of by distillation:

| Example No. | Starting material | Melting point of the end product in °C. | Yield of the end product in % of theory | |
| --- | --- | --- | --- | --- |
| | | | using a hydroxylamine III (as its salt) | using a hydrazine III (as its salt) |
| 15 | Bis-(4-chlorophenyl)-sulfoxide | 93–95 | 68 | 78 |
| 16 | Bis-(4-methylphenyl)-sulfoxide | 57 | 71 | 80 |

We claim:

1. A process for the preparation of a sulfide of the formula $$R^1-S-R^2 \qquad \text{I}$$

where $R^1$ and $R^2$ can be identical or different groups and each is alkyl of 1–8 carbon atoms, cycloalkyl of 5–8 carbon atoms, aralkyl or alkylaryl of 7–12 carbon atoms, or phenyl or chlorophenyl, or where $R^1$ and $R^2$ as alkylene groups together with the adjacent sulfur atom also form a 5-membered or 6-membered heterocyclic ring, each of the above groups being unsubstituted or substituted by oxo, chloro, nitro, cyano or alkyl or alkoxy of 1–7 carbon atoms each, which process comprises:

reducing a sulfoxide of the formula $$R^1-\overset{\overset{\displaystyle O}{\|}}{S}-R^2 \qquad \text{II}$$

where $R^1$ and $R^2$ have the above meanings, by reacting it with an amine derivative of the formula $$H_2N-XR^3 \qquad \text{III}$$

where X is oxygen or $$\overset{H}{\underset{|}{-N-}},$$

and $R^3$ is hydrogen, a sulfonic acid group or an acyl group of a carboxylic acid, or with its ammonium salt, the carbonyl groups which may be present in $R^1$ and $R^2$ being converted to ketoximes in the case in which $R^3$ is hydrogen and X is oxygen, and to the hydrazones in the case in which $R^3$ is hydrogen and X is $$\overset{-N-}{\underset{H}{|}}.$$

2. A process as claimed in claim 1, wherein the reaction is carried out using from 1 to 4 equivalents of starting material III, or of its ammonium salt, per mole of starting material II.

3. A process as claimed in claim 1, wherein the reaction is carried out at from 20° to 150° C.

4. A process as claimed in claim 1, wherein the reaction is carried out at from 55° to 145° C.

5. A process as claimed in claim 1, wherein the reaction is carried out using a solvent which is inert under the reaction conditions.

6. A process as claimed in claim 5 wherein the reaction is carried out in a solvent which is inert under the reaction conditions, using from 1 to 4 equivalents of starting material III, or of its ammonium salt, per mole of starting material II, and at a temperature of from 20° to 150° C.

7. A process as claimed in claim 6 wherein the reaction is carried out at from 55° to 145° C.

8. A process as claimed in claim 6 wherein the starting material III is the unsubstituted hydrazine $H_2N-NH_2$ or hydroxylamine $H_2N-OH$, or ammonium salts thereof.

9. A process as claimed in claim 6 wherein the starting material II is dimethyl sulfoxide.

10. A process as claimed in claim 6 wherein the starting material II is di-n-propylsulfoxide.

11. A process as claimed in claim 6 wherein the starting material II is di-isopropylsulfoxide.

12. A process as claimed in claim 6 wherein the starting material II is di-n-butylsulfoxide.

13. A process as claimed in claim 6 wherein the starting material II is di-tert.-butylsulfoxide.

14. A process as claimed in claim 6 wherein the starting material II is tetramethylensulfoxide.

15. A process as claimed in claim 6 wherein the starting material II is dibenzylsulfoxide.

16. A process as claimed in claim 6 wherein the starting material II is 3,3-dimethyl-1-methylsulfinyl-2-butanone.

17. A process as claimed in claim 6 wherein the starting material II is 2-methylsulfinylacetophenone.

18. A process as claimed in claim 6 wherein the starting material II is methylphenylsulfoxide.

19. A process as claimed in claim 6 wherein the starting material II is diphenylsulfoxide.

20. A process as claimed in claim 6 wherein the starting material II is bis-(4-chlorophenyl)-sulfoxide.

21. A process as claimed in claim 6 wherein the starting material II is bis-(4-methylphenyl)-sulfoxide.

* * * * *